United States Patent [19]

Koros et al.

[11] Patent Number: 5,578,052

[45] Date of Patent: Nov. 26, 1996

[54] INSULATED LAPAROSCOPIC GRASPER WITH REMOVABLE SHAFT

[76] Inventors: Tibor Koros; Gabriel Koros, both of 610 Flinn Ave., Moorpark, Calif. 93021

[21] Appl. No.: 317,307

[22] Filed: Oct. 3, 1994

Related U.S. Application Data

[63] Continuation-in-part of Ser. No. 967,086, Oct. 27, 1992, Pat. No. 5,352,235.

[51] Int. Cl.$^6$ ................................................. A61B 17/00
[52] U.S. Cl. ................................................. 606/174; 606/51
[58] Field of Search ................................. 606/51, 52, 170, 606/174, 205–211; 128/750–755

[56] References Cited

U.S. PATENT DOCUMENTS

| | | | |
|---|---|---|---|
| 5,174,300 | 12/1992 | Bales et al. | 606/174 |
| 5,282,800 | 2/1994 | Foshee et al. | 606/52 |
| 5,330,502 | 7/1994 | Hassler et al. | 606/174 |
| 5,352,235 | 10/1994 | Koros et al. | 606/174 |

*Primary Examiner*—Michael Powell Buiz
*Assistant Examiner*—William Lewis
*Attorney, Agent, or Firm*—Richard D. Slehofer

[57] ABSTRACT

A laparoscopic instrument is formed by a removable shaft combination portion separable from a housing. The housing portion includes a pair of handles, a quick-release button, a clutch to quickly rotate the shaft during use, and a releaser. The socket is attached to the proximal handle. The shaft combination has a center shaft, a slotted outer shaft and a shaft cover insulator. The center shaft has a pair of graspers at the distal operating end. The other end of the center shaft has an anchor point for engaging with the socket at the other end of the instrument. The socket holds the end of the center shaft and causes the shaft to reciprocate slightly in response to the surgeon closing or opening the pair of handles. The graspers close or open in response to the squeezing action by the surgeon. The socket has a quick-release button and the housing has a release to allow the entire shaft combination to be quickly removed from the rest of the instrument, and cleaned or replaced with another shaft combination. The instrument does not have to be disassembled. The clutch allows the surgeon to quickly change the angular orientation of the graspers during the operation. A thumb wheel forming part of the clutch can be easily turned to make the adjustment. The instrument has a plug for connecting to an electric cord to allow the instrument to be used in cauterization techniques. Other than the grapsers, the exposed parts of the instrument are fabricated from an non-electrical conductive material to prevent electrical shock.

7 Claims, 3 Drawing Sheets

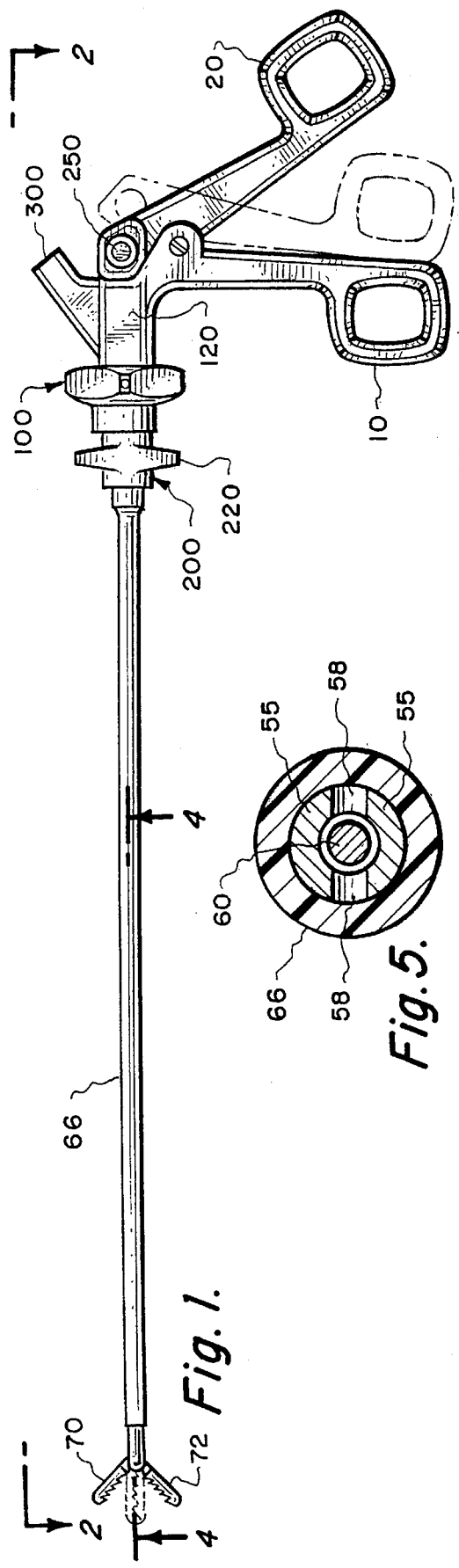
Fig. 1.
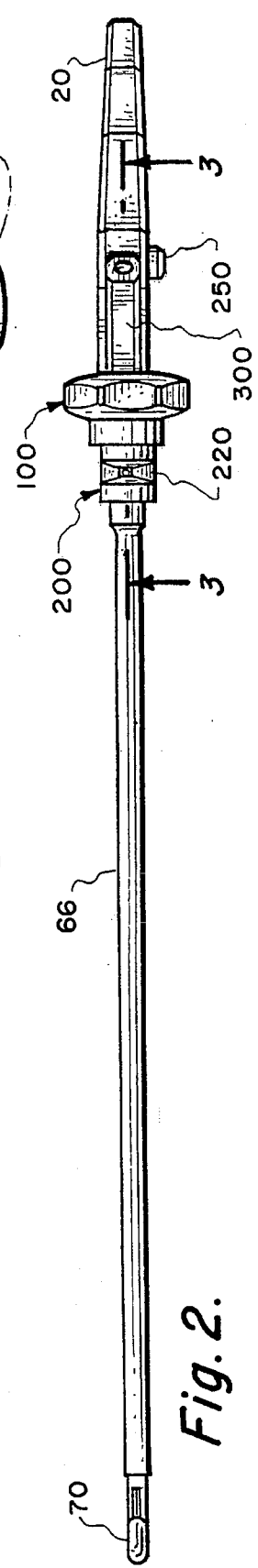
Fig. 2.
Fig. 5.
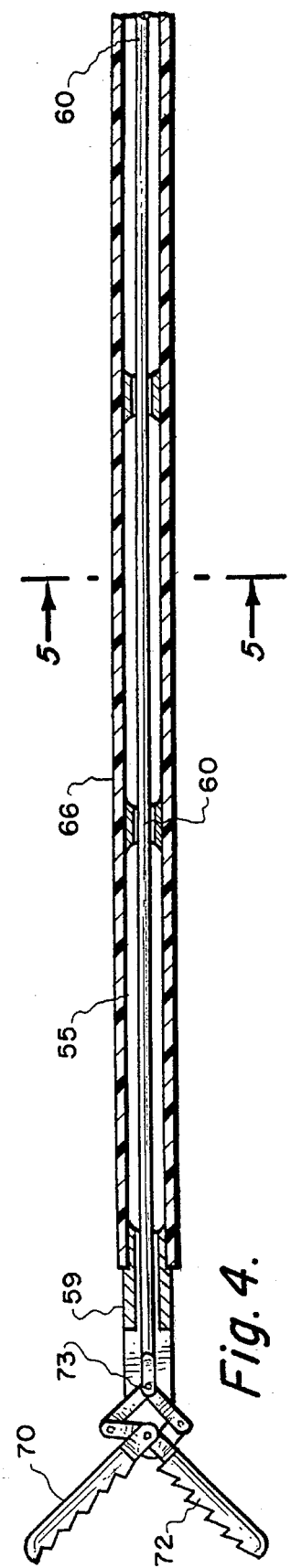
Fig. 4.

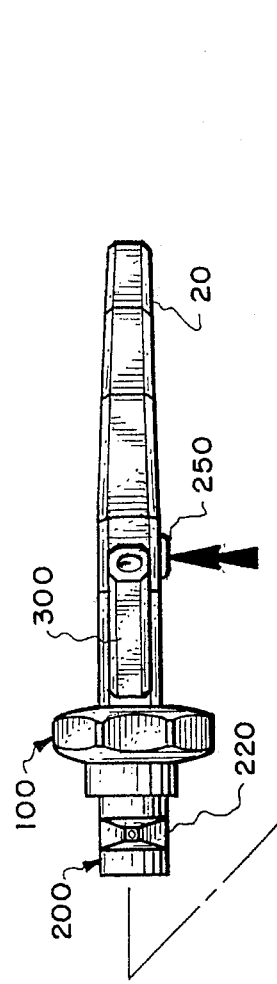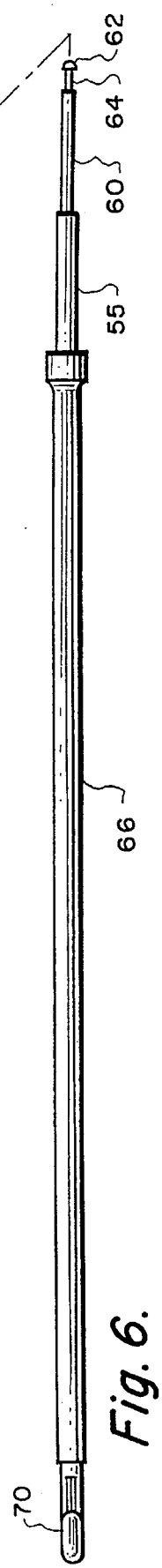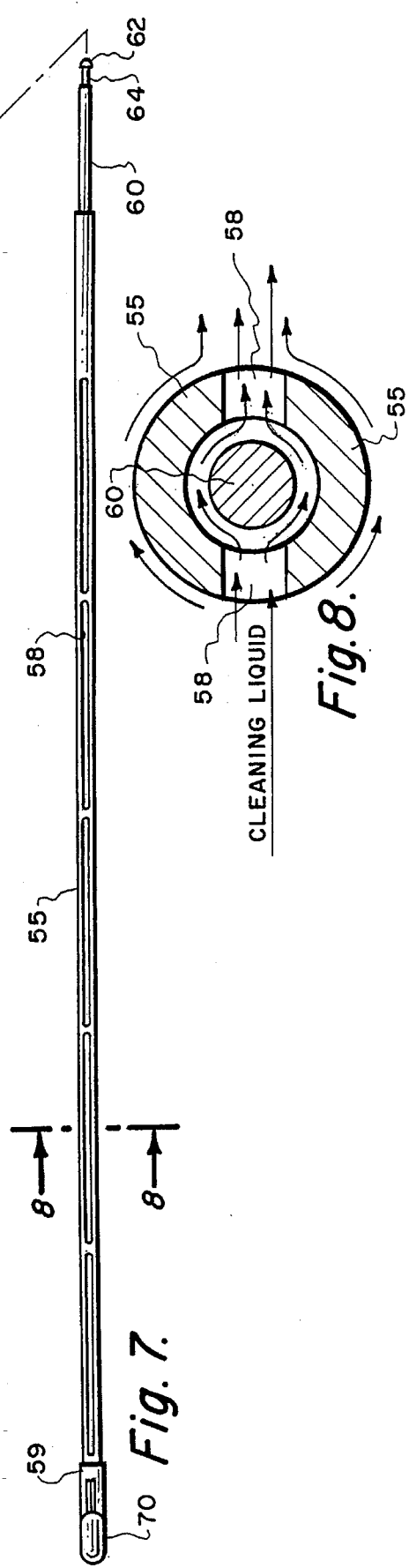

INSULATED LAPAROSCOPIC GRASPER WITH REMOVABLE SHAFT

CROSS REFERENCE TO RELATED APPLICATIONS

This is a continuation-in-part of patent application Ser. No. 07/967,086, which was filed on Oct. 27, 1992, issued on Oct. 4, 1994 as U.S. Pat. No. 5,352,235.

BACKGROUND OF THE INVENTION

1. Field of the Invention

The present invention pertains to the following areas of technology:

SURGERY—Medical and laboratory Equipment; hand-held or manipulated surgical instrument or tool for medical or laboratory use; surgical instrument used in laparoscopic surgery, for example, gall bladder surgery.

2. Description of the Prior Art:

U.S. Pat. No. 4,174,715 issued to Hasson discloses a multi-pronged laparoscopy forceps.

U.S. Pat. No. 3,834,392 issued to Lampman et. al. discloses a complete laparoscopy system for female sterilization by tubal ligation.

Laparoscopic cholecystectomy is the term used to describe the removal of the gall bladder through a minimally invasive surgical technique. Several operations that once required an open incision of several inches can now be done by inserting a tiny video camera and microscopic instruments through small half-inch abdominal openings.

The gallbladder stores bile, which aids in the digestion of fats. Gallstones can form in the gallbladder causing inflammation of the gallbladder and blockage of the bile duct leading to the small intestine. Either condition can cause severe pain in the abdomen, accompanied by nausea and vomiting. Some experimental procedures deal with fracturing the gallstones with sound waves or dissolving the stones with chemicals. The most reliable treatment still available is surgical removal of the gallbladder. Patients can live without their gallbladders. The liver produces the bile, which continuously drips into the small intestine via the bile duct. The gallbladder stores concentrated bile as a backup in case the body needs extra bile after the patient eats a meal. The gallbladder connects to the bile duct. The absence of a gallbladder does not interfere with normal digestion. Conventional surgery requires a lateral 8-inch incision across the stomach, a six-day hospital stay, and at least a one-month recovery. The operation results in considerable postoperative pain and scarring. The new endoscopic procedure for gallbladder removal requires less invasive surgery, reducing the patient's discomfort, scarring, and reduced hospital stay.

The second most common laparoscopic procedure is hernia repair. A hernia is a weakness or tear in the abdominal wall. Some people are born with potential weakness, and when they lift a heavy object, tension forces the abdominal contents through the weakness or tear in the wall. Traditional hernia repair entails an incision in the groin, accompanied by two to six weeks recovery time. Laparoscopic techniques can now be done on an outpatient basis. A mesh is placed between the peritoneal lining and the muscles of the abdominal wall to reduce tension and eliminate the bulge. There is no open incision.

Splenectomy is the term used to remove the patient's spleen. The spleen is an organ designed to help fight infection in the body. But occasionally, the spleen can attack blood platelets. Hodgkin's disease may also require a splenectomy.

Laparoscopic techniques are also used for the following conditions: appendectomy; hiatal hernia repair; enterolysis for adhesions; and vagotomy.

SUMMARY AND OPERATION OF THE INVENTION

The present invention is a surgical instrument and is used in laparoscopic surgical techniques. Laparoscopy is a relatively new surgical procedure as described in the Background of the Invention. The surgical technique is used in the abdominal area. the term is derived from the Greek word for lap meaning flank. In the typical laparoscopic procedure, a trocar which is a tube with a pointed needle at one end, is inserted into the abdominal area through the navel. This point of entry is used to minimize any scaring. Small lateral incisions are also required to provide entry for other instruments including a miniature television camera or an optic light tube to allow the surgeon to view the inside of the abdominal cavity while the operation is in progress. This procedure is also used for diagnostic purposes and is used to enter the abdominal cavity to visually examine the internal organs. The abdominal cavity has to be expanded like a balloon to provide an area for the surgeon to work in. This is accomplished by the introduction of pressurized carbon dioxide gas through the trocar. The trocar has a valve on the exterior portion to attach to a pressurized carbon dioxide gas line of some type. The pressurized carbon dioxide gas enters through the trocar and into the abdominal cavity to expand the cavity. The hollow tube part of the trocar is used to allow the shaft of the laparoscopy instrument to be inserted. A seal at the exterior end of the trocar prevents the carbon dioxide gas from escaping.

The present invention is a laparoscopy instrument approximately 18 inches in length and about 5 inches in height. It has a grasper at its distal end, and a pair of handles at its proximal end. The shaft portion is about 3/16 inches in diameter. The purpose of this instrument is to provide a means for the surgeon to grasp or tear away a piece of organ or body tissue within the area being operated on, and also to cauterize a portion of tissue by passing an electrical current through the instrument at the graspers to cause an electrical arcing and therefore heat at this point to burn or cauterize body tissue. The end of the shaft combination can either have a grasper, a pair of jaws, or a cutter, which will close when the surgeon squeezes the pair of handles located at the proximal end of the instrument. An outer hollow shaft houses a movable inner center shaft, which has the graspers at its distal end and an anchor point at its proximal end. A removable and replaceable outer hollow plastic tube encases most of the inner and outer shaft pair to electrically insulate the shaft. The movable center shaft can move slightly back and forth in the hollow middle shaft in a limited response to the surgeon squeezing the pair of handles. The movement opens and closes the graspers as illustrated in hatched lines in FIG. 1. The proximal handle is shown in broken lines at the position where the graspers are closed. The graspers are also shown in hatched lines in the closed position. The graspers are shown in the open position in FIG. 4. The distal handle has an integral housing mounted towards the top of it. The other handle has a socket with a quick release button integrally mounted at the top of the handle. The socket receives and holds the ball end of the movable shaft to lock and maintain the end of the shaft in the socket. It also allows the shaft to be released quickly by simply depressing a release button to allow the entire shaft combination to be removed from the instrument. A locking means adjacent the thumb wheel locks the inner and outer shaft in place and prevents the shaft from moving by itself unless the lock is released temporarily by pushing towards the handle with the index finger and middle finger. The release cylinder has a pair of radial and opposed wings where the index finger and middle finger of the same hand will easily fit. Unless the quick-release button is depressed, the socket grasps and maintains the end of the shaft and secures it while yet allowing the shaft to rotate when the thumb wheel is turned by the surgeon. The outer hollow shaft is stationary relative to the movable central solid shaft. When the handles are squeezed together, the pair of graspers, jaws or cutting blades function similar to a pair of scissors closing together. Both graspers have jointed toggle ends where each connects to the distal end of the reciprocative inner shaft. The distal end of the outer shaft has an anchor point for a pivot pin so that the proximal ends of the graspers can open and close about the pivot point. The graspers are in effect squeezed together as the inner shaft is being pulled towards the proximal end of the instrument. This retraction or pulling is accomplished by the socket grasping the proximal end of the inner shaft in response to the handles being squeezes together by the surgeon during the operation. Sufficient clearance is provided at the distal end of the shaft combination to allow the graspers to be fully open when the handles are at the maximum spread apart position. When the inner shaft is retracted, the graspers close. This is the function of the instrument, that is, to grasp a piece of tissue during the operation so that the surgeon can manipulate the instrument and the grasped tissue.

Another novel feature of the present invention allows the surgeon to change the orientation of the graspers relative to the instrument. This is accomplished by a clutch means illustrated as a thumb wheel. The thumb wheel is secured to the upper end of the distal handle and at the proximal end of the shaft combination. The surgeon turns the thumb wheel to change the angular orientation of the graspers. A locking and release means with a rotatable cartridge, are also secured to the upper end of the distal handle. The combination is located distally relative to the clutch means. The upper end of the distal handle is integral with a stationary hollow cartridge and has the appearance of a pistol. The stationary cartridge has attached to it a rotation means for rotating the graspers on the shaft. stationary cartridge remains stationary while the rest of the subassembly which comprises the shaft combination, the rotatable cartridge, and the thumb wheel rotate the shaft and therefore the graspers in about 5 degree increments either clockwise or counterclockwise. The upper portion of the proximal handle is secured to the upper portion of the distal handle. The two handles are pivotally secured to one another by a jeweler's screw. Each handle has a ring at its bottom for allowing the surgeon to grasp the handles like a pair of scissors. The upper end of the proximal handle also has a mounting means. The mounting means is a socket having a quick-release button mounted on the top of the proximal handle. The bore in the socket is in an axial alignment with the bore of the inner central shaft so that the ball end of the inner shaft can enter and pass through the bore of the socket. The quick-release button on the socket secures and locks the ball end of the inner shaft but it still permits the angular orientation of the graspers to be changed by rotating the thumb wheel.

Another novel feature of the present invention allows the movable inner central and outer shaft combination containing the graspers to be quickly removed and replaced with another shaft and different type of tip to increase the versatility of the present invention. This is illustrated in FIGS. 6 and 7. The present invention can be quickly disassembled, cleaned, sterilized, and reassembled for the next operation. It can also be easily repaired or refurbished at minimal cost. By simply depressing the quick-release button in the socket mounted at the upper end of the proximal handle, and then depressing the locking means, the entire shaft combination can be removed from the rest of the instrument by pulling on the grasper end and pulling out the shaft combination from the handle assembly. A replacement shaft assembly having the same dimensions can then be quickly inserted in the handle assembly and pushed into the socket and secured therein. The instrument is ready to be used again with another shaft combination and attached graspers. The disposable outer plastic insulating tube is fabricated from plastic and is intended for single use only. The outer insulating tube acts as an electrical insulator to prevent electrical arcing along the shaft. By replacing the outer insulating tube after each use of the instrument, the surgeon is assured that no arcing will take place along the shaft. The center shaft and middle shaft combination having the graspers at the distal is reusable. The center solid shaft is coaxially aligned in the outer hollow shaft. The outer hollow shaft fits snugly in the bore of the outer plastic tube. The main purpose of the outer plastic tube is to insulate the metal cartridges and the inner central shaft. The inner shaft is solid and has the graspers at the distal end and the ball attachment at the proximal end. The outer shaft and the center shaft are fabricated as a one-piece unit and are not separable. Five pairs of opposed elongated longitudinal slots are cut in the wall of the outer shaft. The slots are illustrated in FIG. 7. The five pairs of opposed slots allow cleaning fluid to flow through the spaces between the center shaft and outer shaft to thoroughly clean the shaft combination for reuse. The path of the cleaning fluid flowing through the opposed slots is illustrated in FIG. 8. It is absolutely essential that the shaft combination be thoroughly cleaned and sterilized for the next operation. Serious staph infections result in hospitals even when the operating room and surgical instruments are sterile. Surgical instruments that are not thoroughly cleaned and sterilized greatly increase the chance of post operative infection, which cannot be tolerated.

Yet another novel feature of the present invention is the angular orientation of the two handles. This unique angular orientation results in the outer hollow barrel remaining stationary while the graspers or snippers are being pulled into the shaft during the cutting or grasping stages of the operation. The surgeon is better able to control the cutting, gripping, grasping or pulling activity because only the tips move. When the handles are squeezed together by the surgeon during the operation, the socket is pulled proximally relative to the stationary outer shaft. The outer hollow shaft remains stationary while the graspers are grasping tissue.

The present invention allows electrical current to be passed through to the graspers or cutting tips. The present invention can be described as a monopolar electrocautery laparoscope. The present invention can be used in a cauterization procedure such as in tubal ligation. An electrical current flows to the graspers or tips allowing electrical current to burn or cauterize the target tissue in the abdominal cavity, as selected by the surgeon. The instrument must be electrically insulated to protect everyone including the surgeon from shock. This is accomplished by having the outer portions including the pair of handles, the thumb wheel, the outer hollow shaft, and the barrel fabricated from a rigid plastic material that is non-conducting. An acceptable plastic is FDA approved no. 6 plastic. A means for plugging in an electrical cord, and an electrical conduction to the metallic graspers or cutting blades are necessary. The quick release button securement means is integral with the top of the proximal handle.

Accordingly, it is an object of the present invention to provide an electrically insulated laparoscopy instrument which can be used to cauterize a patient without creating electrical shock to the patient or the surgeon while using the instrument during the operation. The graspers act as the ground for the flow of electricity. The current flows from the tip of the instrument to the area adjacent the placement of the tip. Heat is generated by the electricity at this point causing cauterization.

It is another object of this invention to provide a disposable plastic outer insulator for covering the shaft combination to insulate the shaft from any dangerous electrical arcing during the operation.

Expressed another way, a laparoscopic instrument is formed by a removable shaft combination portion separable from a housing. The housing portion includes a pair of handles, a quick-release button, a clutch to quickly rotate the shaft during use, and a releaser. The socket is attached to the proximal handle. The shaft combination has a center shaft, a slotted outer shaft and a shaft cover insulator. The center shaft has a pair of graspers at the distal operating end. The other end of the center shaft has an anchor point for engaging with the socket at the other end of the instrument. The socket holds the end of the center shaft and causes the shaft to reciprocate slightly in response to the surgeon closing or opening the pair of handles. The graspers close or open in response to the squeezing action by the surgeon. The socket has a quick-release button and the housing has a release to allow the entire shaft combination to be quickly removed from the rest of the instrument, and cleaned or replaced with another shaft combination. The instrument does not have to be disassembled. The clutch allows the surgeon to quickly change the angular orientation of the graspers during the operation. A thumb wheel forming part of the clutch can be easily turned to make the adjustment. The instrument has a plug for connecting to an electric cord to allow the instrument to be used in cauterization techniques. Other than the grassers, the exposed parts of the instrument are fabricated from an non-electrical conductive material to prevent electrical shock.

BRIEF DESCRIPTION OF THE DRAWINGS

FIG. 1 is a left side elevational view of the present invention.

FIG. 2 is a top plan view of FIG. 1. taken along the line 2—2 of FIG. 1.

FIG. 4 is a longitudinal horizontal sectional view of the shaft portion taken along the line 4—4 in FIG. 1.

FIG. 5 is a transverse sectional view taken along the line 5—5 in FIG. 4.

FIG. 6 is an exploded view showing the two-piece shaft and plastic tube combination and how it is inserted into the handle portion of the invention.

FIG. 7 is exploded view of the triple shaft combination showing how the center and middle single piece metal shaft is inserted in the outer hollow insulated plastic shaft. The outer hollow is disposable and is discarded after one operation. The metal middle-center shaft combination is separated from the outer plastic tube and is cleaned for reuse.

FIG. 8 is a transverse sectional view taken along the line 8—8 in FIG. 7 illustrating how cleaning fluid flows through the opposed slots in the middle shaft to thoroughly clean the middle and center shaft combination for reuse.

DETAILED DESCRIPTION OF THE PREFERRED EMBODIMENT

Figure 3:
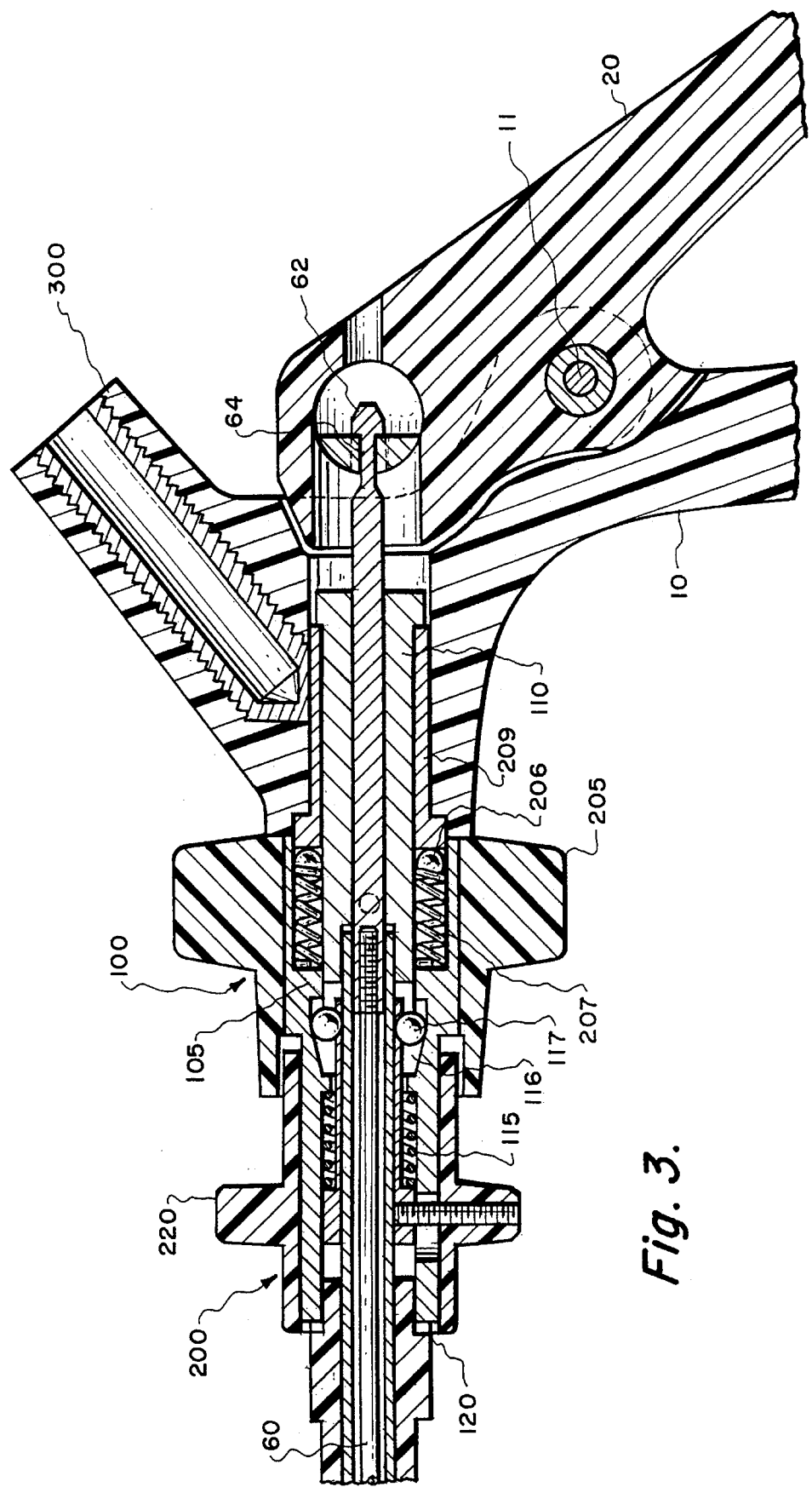
FIG. 3 is a vertical longitudinal sectional view taken along the line 3—3 in FIG. 2 illustrating the handles and barrel portion in an at-rest open position.

The present invention will now be discussed in greater detail. FIG. 1 is the left side elevational view illustrating the graspers at the left or distal end and the pair of handles at the right or proximal end. The instrument is about 16 to 18 inches long and about 4 inches high. The major components comprising the present invention are: The shaft 55 is hollow throughout and has both ends open to house the inner solid shaft 60 and to allow the inner shaft 60 to reciprocate therein. The distal end of the inner solid shaft 60 has grasping means illustrated as a pair of opposed serrated graspers labelled 70 and 72. The pair of graspers forms a Y-shaped configuration with the end of the inner central shaft 60. The pair of graspers is secured to the end of the shaft 60 with a pin 73. The movable shaft 60 has a securement means at its right or proximal end. The securement means is illustrated as a ball-like tip 62. It is formed by a annular groove 64 cut inboard from the proximal end of the movable shaft 60. These features are clearly illustrated in FIG. 3. The securement means is used to engage and lock the proximal end of the movable shaft 60 to the quick-release socket 250.

The socket, collectively labelled 250, is clearly illustrated in FIG. 3. The socket 250 is mounted on the upper portion of the proximal handle 20. The socket 250 has an axial bore passing therethrough, which is axially alignable with the movable shaft 60. The socket 250 includes a spring loaded quick release button and lock combination. The opening in the button is aligned with the bore so that the ball end 62 of the movable shaft 60 can pass through the bore and into the socket. A means is included for maintaining the grooved portion 64 of the shaft 60 in the button 250. This locks the ball end 62 of the shaft 60 in place. By depressing the button, the ball end 62 of the shaft 60 can be removed from the socket 250. FIG. 6 illustrates the depressing of the quick release button by means of a vertical arrow pointed at the button during the removal of the ball end 64 of the shaft 60 from the socket 250. Unless the button is depressed, however, this locking means still allows the shaft 60 and ball end 62 to rotate even while the ball end 62 is locked in place as illustrated in FIG. 3. As the socket 250 travels distally and proximally in response to the handles 10 and 20 being squeezed together or spread apart by the surgeon, the movable inner shaft 60 reciprocates proximally or distally the same amount. The whole purpose of this reciprocal distal-proximal lengthwise movement of the movable shaft 60 is to cause the grasping means 70 to open and close at the distal end of the shaft 60.

The clutch or locking means, collectively labelled 200, and the rotation means, collectively labelled 100, will now be discussed in greater detail. The clutch and rotation means are mounted to the distal end of the housing 120 integral with the upper end of the distal handle 10.

The rotation means 100 and clutch means 200 combination include the following major subcomponents; a hollow cylinder-shaped distally positioned internal hollow metal cartridge 105; a hollow cylinder-shaped proximally positioned internal hollow metal cartridge 110; a thumb wheel 205; a coil spring 207; a coil spring 115 and a cone-shaped cavity 116 with movable ball bearings 117. Radially cut teeth 120 are located on the distal face and circumjacent the bore of the cartridge 105.

The thumb wheel 205 has a plurality of radially spaced apart rounded projections with semicircular indentations formed between the projections. The thumb wheel surface is designed for easy gripping by the surgeon while he or she is wearing latex gloves and using the present invention during an operation. The projections form an array of nubs.

The thumb wheel 205 has two stepped bores forming the overall bore. Both bores are in a spaced apart axial alignment with each other. The smaller bore is located proximally in the overall bore. The smallest bore is the same diameter as the bore in the proximal portion of the distal cartridge.

By simply turning the thumb wheel 205 a few degrees at a time, the angular orientation of the graspers 70 is changed the same number of degrees. If the surgeon rotates the thumb wheel 205 a quarter of a turn the angular orientation of the graspers 70 is changed ninety degrees. If the surgeon rotates the thumb wheel 205 one-half of a turn, the angular orientation of the graspers 70 is changed 180 degrees. Since the thumb wheel 205 can rotate clockwise or counterclockwise, the surgeon need only turn the thumb wheel a half a turn at most to set the angle of the graspers to any desired angle.

The pair of handles will now be discussed in greater detail. The pair of handles are labelled 10 and 20. The distal handle 10 has a finger ring at its bottom and an integral housing 120 at its upper end. As previously discussed, the integral housing is for mounting the rotation means and the clutch or locking means for the shaft combination. The two handles can be pivotally secured with a set screw 11. The proximal handle forms a mirror image with the distal handle 10 up to the area where the two are pivotally connected to one another. The drawings illustrate both handles in an open position. If one were to squeeze both handles together so that they touch each other, the mirror image relationship could be readily observed.

Because the laparoscopic procedure is being done inside the patient, the surgeon cannot actually see what he is grasping with the instrument. He must rely on the images formed on the television monitor that are relayed from a tube or miniature camera in the patient. Because the instrument does not move during the cutting process, the field of view on the screen keeps the graspers in view so that the image transmitter does not have to be realigned for the image receiver.

The handles 10 and 20, outer shaft 55, socket 250, housing 120, thumb wheel 200, and locking and clutch means 100 are all fabricated from an electrical insulating type of material such as FDA approved plastic no. 6. The proximal handle 20 has an electrical receiving plug means 300 so that the tip of an insulated electrical conducting cord can be plugged into the instrument.

Laparoscopic procedures commonly include cauterization where the tissue is seared or burned with a hot tip. Tubal ligation involves cauterization of the fallopian tubes or oviducts to sterilize a female patient. The exposed metal graspers 71 and 72 extending from the distal end of the shaft combination 50 act as an electrical conducting tip when an electric cord is plugged into the instrument to pass electricity to the tips. The electric current travels to the tissue adjacent the metal graspers 71 and 72 causing an electric arc and resultant heat. The electrical insulating material forming most of the instrument prevents electric shock to the surgeon or the patient. When the electric cord is not plugged into the instrument or if the cord is switched off, the instrument can be used in the same manner as conventional laparoscopic instrument.

The rotatable shaft combination, collectively labelled 50, includes an outer hollow tubular shaft 55, an inner solid cylindrical shaft 60, and an exterior hollow tubular shaft electrical insulator cover 66. The major components of the shaft combination 60 are clearly illustrated in FIGS. 6 and 7. The outer hollow tubular shaft 55 has a series of five opposed slotted openings 58 in the wall of the tubular opening 55. The outer hollow tubular shaft 55 has an enlarged cylinder head 59 at its distal end for holding the graspers and the graspers moving toggle parts which cause the graspers to open and close in response to the surgeon squeezing the pair of handles. The proximal end of the head also functions as a stop for the distal end of the plastic cover 66. FIG. 7 clearly illustrates the tubular shaft 55 unit having the slotted openings 58, the inner solid shaft 60, and the graspers 70. The inner shaft 60 is permanently positioned axially within the tubular shaft 55. The distal end of the inner solid shaft 60 has grasping means collectively labeled 70. The grasping means is illustrated as a pair of opposed jaws labelled 71 and 72. The shaft combination 50 can be removed from the housing portion of the instrument as illustrated in FIG. 6. The shaft and the rest of the instrument can be cleaned and sterilized and assembled for reuse. A replacement shaft can also be quickly inserted in the instrument.

The circumference of the thumb wheel 205 is shaped like a star with circular indentations formed between the points of the star. The star surface is designed for easy gripping by the surgeon while he is wearing latex gloves while performing an operation. The points of the star form a series of nubs. The graspers extending from the distal end of the shaft combination cannot change their angular orientation unless the inner shaft is rotated. The thumb wheel and the associated parts function like a rotatable wheel to allow the inner shaft to rotate to allow the surgeon to change the orientation of the graspers. By simply turning the thumb wheel a few degrees at a time, the angular orientation of the graspers are changed the same number of degrees. The movement between the ball bearings 206 and depressions in the face of a cylinder sleeve 209 causes a clicking sound while turning the thumb wheel. This audible clicking sound helps the surgeon to judge how far to turn the thumb wheel. After using the instrument for some time, the surgeon can judge the angular change by associating it with the number of clicks. The coil spring 207 forces the thumb wheel against the sleeve 209 to make a clicking noise as the thumb wheel is rotated.

The shaft combination can be quickly removed. The button 250 is first depressed. The clutch or locking means 200 has a pair of radial and opposed wings 220 where the index finger and middle finger of the same hand will easily fit. The wings are pulled to release the shaft combination from the housing. The plastic tube is disposable for each operation. Other laparoscopic instruments have the shaft covered with insulating vinyl. If a small scratch in the vinyl occurs exposing the metal shaft, electrical arcing could take place at the scratch during cauterization. This could cause a hole to burn in the patient's intestines. The surgeon would not be aware of the burn hole, until after the operation when the patient develops severe infection. The plastic tube prevents this dangerous accident from happening.

Obviously, many modifications and variants of the present invention are possible in light of the above teachings. It is therefore to be understood that the full scope of the invention is not limited to the details disclosed herein, but may be practiced otherwise than as specifically described.

What is claimed is:

1. A monopolar laparoscopic electrocautery laparoscope surgical instrument having an insulated removable shaft, which comprises:

a rotatable combination shaft having a proximal end and a distal end;

said rotatable shaft combination comprising:

an outer hollow shaft having at least one slotted opening in its wall for allowing said shaft to be cleaned thoroughly after use;

an inner shaft slidably positioned axially in said outer hollow shaft;

grasping means at said distal end of said inner shaft;

anchor means at said proximal end of said inner shaft;

a removable and disposable shaft cover covering and insulating the body of said shaft combination other than said grasping means for preventing electrical arcing when the instrument is used as a cauterizer during use;

release means on said instrument for allowing said shaft combination and said removable and disposable shaft cover to be removed from said instrument for cleaning said shaft combination and for replacing said removable and disposable shaft cover with a new shaft cover;

a pair of distal and proximal squeeze handles pivotally secured together;

means on said handles and said instrument for receiving an electric cord and transmitting electric current to said grasping means on said distal end of said inner shaft;

means on said proximal handle for releasably securing said anchor means at said proximal end of said inner shaft;

said pair of squeeze handles, said shaft release means, and said housing being fabricated from non-electrically conductive material for protection against electric shock whenever electric current is passed through said instrument.

2. The surgical instrument as recited in claim 1 wherein said means attached to said proximal handle for releasably securing said anchor means at said proximal end of said shaft includes a socket with a quick-release button.

3. The surgical instrument as recited in claim 2 wherein said anchor means at said proximal end of said shaft includes a ball-like tip so that said socket will secure said tip and yet allow said inner and outer shaft combination to rotate and allow said inner shaft to reciprocate when desired, and allow said shaft combination to be removed by pressing said quick-release button and pulling said shaft combination out from said housing of said instrument.

4. The surgical instrument as recited in claim 1 wherein said pair of distal and proximal squeeze handles pivotally secured together include angled shanks and braces so that when said pair of handles are squeezed together by the surgeon during the operation, said socket is pulled proximally relative to said stationary hollow shaft whereby said hollow shaft and supports remain stationary while said grasping means at said proximal end of said inner shaft are cutting tissue.

5. The surgical instrument as recited in claim 1 wherein said means at said distal end of said inner shaft for grasping includes a pair of graspers, each grasper being secured to said proximal end of said inner shaft with a toggle joint linkage, said graspers closing in response to the surgeon squeezing said pair of handles in order to grasp tissue positioned between said pair of graspers.

6. The surgical instrument as recited in claim 1 wherein said rotatable shaft combination can be removed from said instrument and replaced with another rotatable shaft combination by:

actuating said means on said proximal handle;

actuating said release means on said instrument;

removing said shaft combination from said instrument; and inserting another said shaft combination into said instrument.

7. The surgical instrument as recited in claim 1 further comprising:

clutch means for allowing angular adjustment of said shaft combination to allow angular adjustment of said graspers on said shaft combination.

* * * * *